(12) United States Patent
Näfstadius

(10) Patent No.: US 6,865,254 B2
(45) Date of Patent: Mar. 8, 2005

(54) RADIATION SYSTEM WITH INNER AND OUTER GANTRY PARTS

(75) Inventor: Peder Näfstadius, Taby (SE)

(73) Assignee: PencilBeam Technologies AB, Uppsala (SE)

( * ) Notice: Subject to any disclaimer, the term of this patent is extended or adjusted under 35 U.S.C. 154(b) by 176 days.

(21) Appl. No.: 10/186,629

(22) Filed: Jul. 2, 2002

(65) Prior Publication Data

US 2004/0005027 A1 Jan. 8, 2004

(51) Int. Cl.[7] .............................................. A61N 5/10
(52) U.S. Cl. ........................... 378/65; 378/4; 378/9
(58) Field of Search ..................... 378/65, 4, 15, 378/9; 250/363.03, 363.04, 363.08, 374, 385.1, 214 VT; 313/105 CM, 103 CM, 542, 544, 103 R, 538, 365, 523, 532, 533

(56) References Cited

U.S. PATENT DOCUMENTS

| | | | |
|---|---|---|---|
| 5,473,657 A | * 12/1995 | McKenna | 378/4 |
| 5,673,300 A | 9/1997 | Reckwerdt et al. | |
| 5,751,781 A | 5/1998 | Brown et al. | |
| 6,041,097 A | * 3/2000 | Roos et al. | 378/62 |
| RE37,474 E | * 12/2001 | Hug et al. | 250/363.08 |
| 6,385,288 B1 | * 5/2002 | Kanematsu | 378/65 |
| 6,429,578 B1 | * 8/2002 | Danielsson et al. | 313/105 CM |
| 6,445,766 B1 | * 9/2002 | Whitham | 378/65 |
| 6,617,768 B1 | * 9/2003 | Hansen | 313/103 CM |
| 6,667,482 B2 | * 12/2003 | Von Der Haar | 250/370.11 |

FOREIGN PATENT DOCUMENTS

| | | |
|---|---|---|
| EP | 0 205 720 | 12/1986 |
| FR | 2 728 471 | 6/1996 |
| WO | 00/74779 A1 | 12/2000 |
| WO | 01/60236 A2 | 8/2001 |
| WO | 01/60236 A3 | 8/2001 |
| WO | 02/13907 A1 | 2/2002 |

* cited by examiner

Primary Examiner—Edward J. Glick
Assistant Examiner—Elizabeth Keaney
(74) Attorney, Agent, or Firm—Young & Thompson

(57) ABSTRACT

A radiation machine incorporating a diagnostic imaging system is disclosed. The invention provides a very stable design of the machine by supporting an inner gantry part, including a treatment and diagnostic radiation source and detector, by an outer gantry part at two support locations situated at opposite sides of a treatment volume in a patient to be irradiated. This stable gantry design provides a high rotation speed of the inner gantry part relative the outer gantry part around the target volume, which speed is adapted for the high resolution imaging system. Based on the obtained images, changes and developments in tumor tissue and misplacement of patient may be detected. The images may be compared to a reference image to detect any anatomical or spatial difference therebetween. Based on this comparison the settings of the radiation machine may be adapted accordingly.

13 Claims, 13 Drawing Sheets

CONTROL SIGNAL

RADIATION SYSTEM WITH INNER AND OUTER GANTRY PARTS

TECHNICAL FIELD OF THE INVENTION

The present invention generally relates to radiation systems and in particular such systems incorporating a diagnostic imaging functioning.

BACKGROUND OF THE INVENTION

During the past decades there have been considerable developments within the field of radiation therapy. The performance of external beam radiation therapy accelerators, brachytherapy and other specialized radiation therapy equipment has improved rapidly. Developments taking place in the quality and adaptability of radiation beams have included new targets and filters, improved accelerators, increased flexibility in beam-shaping through new applicators, collimator and scanning systems and beam compensation techniques, and improved dosimetric and geometric treatment verification methods have been introduced.

Furthermore, a number of powerful 3-dimensional diagnostic techniques have been developed, ranging from computed tomography (CT), positron and single photon emission computed tomography (PET and SPECT) to ultrasound and magnetic resonance imaging and spectroscopy (MRI and MRS). Equally important is the increased knowledge of the biological effect of fractionated uniform and non-uniform dose delivery to tumors and normal tissues and new assay techniques, including the determination of effective cell doubling times and individual tissue sensitives, allowing optimization of the dose delivery to tumors of complex shape and advanced stages.

However, one of the weakest links in this development in radiation or radiation therapy treatment has been delivering correct dose to the target volume, including tumor tissues, in a patient. In order to guarantee accurate dose delivery, detailed anatomical information of the tumor, surrounding tissues, organs and bone structures is required. From this information, the target volume with the tumor is defined in the patient body in relation to some reference points or structures, e.g. adjacent bones or standard anatomical reference points used in radiation therapy. During the treatment in a radiation therapy machine, the target volume is then aligned relative the treatment radiation source based on these associated reference points. In other words, an indirect alignment of the target volume is performed, since the position of the reference points and not the actual target volume is used. However, the target volume with the tumor is a fluid structure and its position relative the reference points is not rigid, but may change depending on e.g. posture of the patient, filling degree of bladder, respiratory motion, etc. Therefore, although the reference points are aligned correctly in relation to the treatment radiation source, the target volume may be misaligned.

In addition, during the treatment procedure, the spatial relationship between the target volume and the reference points and the shape and size of the tumor may change, due to loss of weight, changes in the filling degree of bladder and changes in tumor size caused by the already delivered radiation doses. Thus, the received dose in the target volume in a subsequent treatment occasion may differ from an ideal or expected dose. In some extremes, the radiation dose may actually partly or completely miss the target volume and instead hit adjacent tissues and organs. This not only makes the treatment ineffective, but may also harm healthy tissue in the patient.

Today, diagnostic imaging machines have to be used between different treatment occasions to evaluate the dose delivery and detect changes in tumor size and position. However, this is an ineffective and expensive solution, since the patient then has to be moved between different machines, i.e. the diagnostic machines and the treatment machine. In addition, the position and posture of the patient in the machines, most often, are not identical and therefore the position of the tumor relative the reference points differs between the machines.

A method for aligning a patient for radiation treatment in a radiation therapy machine incorporating a computed tomography functioning is shown in U.S. Pat. No. 5,673,300. In a gantry of the radiation therapy machine, an X-ray source collimated to produce a fan beam and an associated detector are arranged to produce tomographic scans of a patient. The gantry also comprises a treatment radiation source emitting a fan beam of high-energy radiation to a target volume in the patient and a dedicated detector adapted to receive the high-energy beam passing through the patient. From an earlier tomographic patient scan, projection images are used to reconstruct a tomographic image. These images are then compared to projection images taken at the time of the radiation therapy to determine a series of offsets of the patient, which may be used to characterize and correct for motion of the patient between the initial tomographic scan, used for treatment planning, and one or a series of subsequent radiation treatment sessions.

The radiation therapy machine in U.S. Pat. No. 5,673,300 divides and irradiates the target volume in a plurality of slices. If the patient moves slightly during the actual dose delivery, a major portion or the whole radiation dose will miss the actual slice. Thus, an incorrect and inefficient radiation delivery is accomplished, possibly irradiating sensitive tissues and organs and causing more harm than good. In addition, due to imperfections of the collimation, scattering of the fan beam causes some radiation to be delivered to the patient out of the intended actual slice. Therefore, the irradiated slices receive too low radiation doses, whereas surrounding tissues and organs receives a too high dose.

In the international application WO 01/60236, a radiation therapy system is disclosed. The system includes a radiation source that moves about a path and directs a beam of radiation towards an object and a cone-beam computer tomography (CT) system. The cone-beam CT system includes an X-ray source that emits an X-ray beam in a cone-beam form towards an object to be imaged and an amorphous silicon flat-panel imager receiving X-rays after passing through the object, the imager providing an image of the object. A computer is connected to the radiation source and the cone-beam CT system, wherein the computer receives the image of the object and based on the image sends a signal to the radiation source that controls the path of the radiation source.

The general L or C shaped gantry of the radiation therapy system in WO 01/60236 is designed for a rotation speed according to recommendations of the International Electromechanical Commission (IEC), i.e. about 1 minute per revolution. The rotational support of the system is provided at one axial end of the body, which together with the heavy weights may cause the gantry arms to elastically deform, especially for a rotation speed faster than 1 minute per revolution. Thus, instead of a pure rotation, the gantry will precess, creating an inaccuracy in the positioning of the radiation head. However, if the cone-beam CT system is to function efficiently much faster rotation speeds than 1 minute per revolution are required. During the 1 minute of revolution, the patient may move considerably, whereby an inaccurate and misleading CT image is obtained.

SUMMARY OF THE INVENTION

The present invention overcomes these and other drawbacks of the prior art arrangements.

It is a general object of the present invention to increase accuracy in radiation therapy treatment.

It is another object of the invention to provide a radiation machine incorporating a diagnostic imaging system Yet another object of the invention is to provide a radiation machine with a stable design to allow gantry rotation speeds adapted for diagnostic imaging.

A further object of the invention is to provide a radiation machine enabling imaging using both a high energy treatment radiation source and a low energy diagnostic energy source.

Still another object of the invention is to provide a radiation machine that automatically may adapt the treatment based on an image determined by the incorporated diagnostic imaging system.

These and other objects are met by the invention as defined by the accompanying patent claims.

Briefly, the present invention involves a radiation machine with a diagnostic imaging system. The radiation machine has a very stable gantry design, making a high rotation speed possible, which in turn is a requirement for obtaining high-resolution images with the imaging system. This stable gantry design is accomplished by dividing the radiation machine into an inner and an outer gantry part, respectively. The inner gantry part is rotatably supported by the outer gantry part at two support locations situated at opposite sides of a treatment volume in a patient to be irradiated. In the inner gantry part, radiation head is arranged, which comprises a treatment radiation source providing treatment radiation or dose package into the target volume. Preferably, in or on the radiation head a diagnostic radiation source is provided. The diagnostic radiation source is arranged to deliver a diagnostic radiation onto the patient, preferably in the vicinity of the target volume, which radiation then is detected by a detector arranged in the inner gantry part. Connected to the detector, a processing means provides an image of the patient (target volume) based on the detected radiation. This image may then be used to identify tissues, organs and structures of interest, including the tumor and associated reference points. From this identified anatomical information, any changes in the tumor tissue, e.g. change in position, size and shape, are detected and used to adapt the treatment accordingly. Any misplacement of the patient on the body-supporting couch in the radiation machine may also be detected by investigating the image. In addition, the image may be compared to a reference image, e.g. from a treatment or dose plan, to find any differences in positioning. Based on such a comparison the position of the patient may be manually or automatically changed, by e.g. adjusting the couch. As a complement, the treatment radiation source may be adapted to consider any detected changes from the expected conditions according to the treatment plan.

The diagnostic imaging system of the invention is preferably a computed tomography (CT) system, and more preferably a cone-beam CT system. The detector is adapted to detect the low energy radiation (photons) of the cone-beam CT system and sends a signal to the processing means based on the detected irradiation. The processing means then computes an 3-dimensional image of the patient, preferably the portion thereof including the target volume, which may be visualized, compared to a reference image or stored. The detector is preferably also adapted to detect the high-energy radiation from the treatment radiation source. With this high-energy radiation, a rather poor contrast portal image is determined, which may be used for e.g. positioning purposes.

The invention offers the following advantages:

Stable gantry design;

High rotation speed of treatment and diagnostic radiation source and detector;

High resolution and accuracy images of the patient;

One and the same detector is used for both portal imaging and diagnostic imaging, reducing the total cost since no dedicated portal imager is needed;

Reduction in total cost and time of a radiation therapy process;

Increased accuracy in the treatment by detecting changes in tumor tissue and any misplacement of the patient; and May provide non-coplanar radiation treatment.

Other advantages offered by the present invention will be appreciated upon reading of the below description of the embodiments of the invention.

BRIEF DESCRIPTION OF THE DRAWINGS

The invention, together with further objects and advantages thereof, will be best understood by reference to the following description taken together with the accompanying drawings, in which.

DETAILED DESCRIPTION OF EMBODIMENTS OF THE INVENTION

Figure 1:
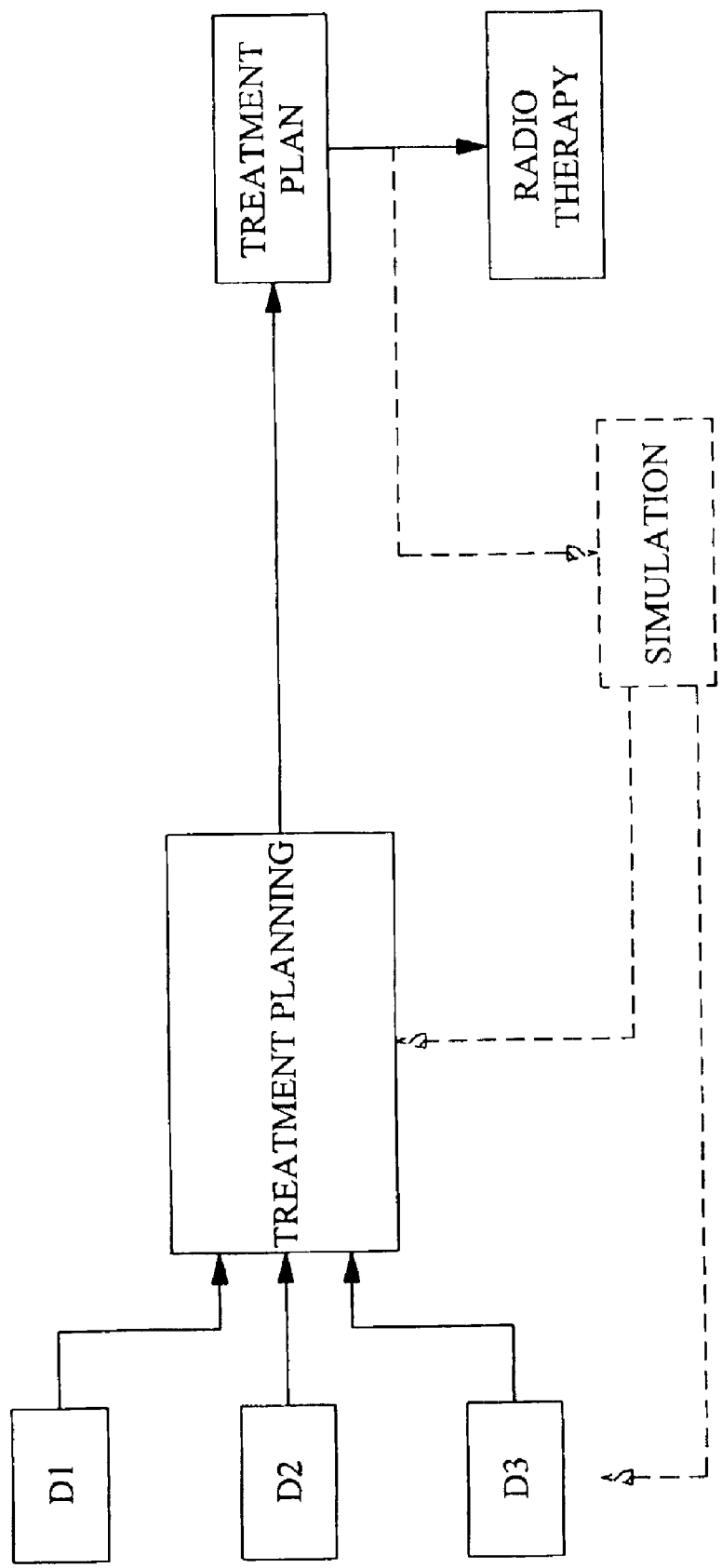
FIG. 1 is a schematic drawing of the main steps in a radiation therapy process.

Throughout the drawings, the same reference characters will be used for corresponding or similar elements.

The invention is generally applicable to a radiation machine. As referred to in the present description, in a radiation machine a dose package or radiation beam, such as a beam of gamma photons, electrons, neutrons, protons or heavier ions, atoms or molecules, is applied to patient. The radiation machine may be employed for curative radiation therapy, i.e. to eradicate a tumor or palliative radiation therapy, where the aim is generally to improve quality of life of the patient by maintaining local tumor control, relieve a symptom or prevent or delay an impending symptom, and not primarily to eradicate the tumor. Yet another application of a radiation machine may be in radiation surgery using a high-energy radiation source.

For a better understanding of the invention, it may be useful to start with a brief introduction of a radiation therapy process with reference to FIG. 1.

Generally, the first step in a radiation therapy process is diagnosing. Different diagnostic machines are employed to obtain anatomical information of a patient, for example to localize a tumor and adjacent tissues and organs. It is normally advisable to use anatomical information D1, D2, D3 from several diagnostic machines, since different imaging techniques give different anatomical information. Therefore, information D1, D2, D3 complement each other and should together give a sufficient picture of the target volume and surrounding tissues.

Based on the measured anatomical information, a treatment or dose planning is carried out. In the treatment planning, the determined anatomical information from the different diagnostic machines is integrated to, as accurately as possible, pinpoint the exact location of the tumor in the patient and detect any organs or tissues that may be affected or should be avoided by the radiation beam in the subsequent radiation therapy treatment. The target volume and the dose to be delivered thereto are defined together with the directions, from which the target volume should be irradiated. The target volume is defined in relation to some identifiable reference points, which may be used to position the patient in the radiation machine.

The result of the treatment planning is a treatment plan, which should include all relevant information for the actual radiation therapy treatment, such as the selected set-up of the radiation therapy machine and its settings. Before the actual radiation therapy treatment, an optional treatment simulation may be performed to test and verify the treatment plan and to determine the positioning of the patient in the radiation machine. Firstly, the patient is positioned as accurately as possible with portal imaging. In portal imaging, the treatment beam itself and a detector is used to get a low contrast image of the patient. From this image the positions of selected reference points may be identified and compared to the corresponding positions in the treatment plan. A deviation therebetween results in a repositioning of the patient until the deviation is below a safety threshold value. In the treatment room, lasers producing laser beams are arranged. The beams cross exactly at the isocenter or the origin of the room coordinate system. When the patient is placed on the couch, the isocenter is inside the body, thus the laser beams can be seen as bright dots on the surface of the skin. Once the correct patient position is obtained, the positions of the bright dots are marked with special ink, which stays in the skin for weeks. Next time the patient is to be positioned, it is sufficient to align the marks with the laser beams.

Furthermore, in the simulation procedure e.g. in vivo dosimetry or related techniques may be used to check the delivered radiation dose in the target volume and/or in adjacent tissues, preferably in organs at risk. If the measured data corresponds to the calculated data in the treatment plan, the actual radiation therapy treatment may be initiated. However, if some deviation between the measured and calculated data is detected and the deviation exceeds a given safety threshold, a change in the treatment planning is performed. This change may in some cases simply be a resetting of parameters but also a larger change in the treatment planning, such as completing the treatment planning with more anatomical information from a new diagnostic measurement. Either way, a new treatment plan is determined, which may be tested and verified in an optional new treatment simulation.

A radiation therapy treatment is then performed with the equipment, set-up and settings specified in the treatment plan. The patient is then positioned or aligned using portal imaging, as described above, and/or laser beams and marks. It is vitally important that the patient is positioned accurately as a misplacement of only a few millimeters may cause damages to adjacent tissues and organs and may make the treatment ineffective. Once the positioning is ready, the beams irradiate the patient according to the treatment plan to deliver the calculated dose in the target volume.

Although, the radiation therapy treatment in the section above has been described in relation to a single treatment occasion, the actual dose delivery is most often fractionated into several, often 20–30 fractions. This means that a total radiation therapy treatment usually extends over a period of days, weeks or in some occasions even months.

A radiation machine according to the present invention incorporates, besides a treatment radiation source, a diagnostic imaging system with diagnostic radiation source, detector and processing means to record and create an image of a patient in the radiation machine. The actual design of the radiation machine provides a very stable gantry, which is a requirement for a high rotation speed. This high rotation speed in turn makes both accurate and high resolution imaging of the patient possible using the diagnostic imaging system.

With the invention, high resolution images of the surroundings of the target volume, including the reference points and sometimes even the tumor tissue itself, are obtained. The measured patient images are then preferably compared to the corresponding anatomical information in the treatment plan. Based on a comparison therebetween, the position of the patient may be accurately adapted and corrected in the radiation machine.

Furthermore, the development of the tumor tissue during the treatment may be monitored to detect any changes in tumor shape, size and position. Any detected changes may then be used to adapt the treatment plan accordingly to achieve an efficient and safe treatment.

Figure 2:
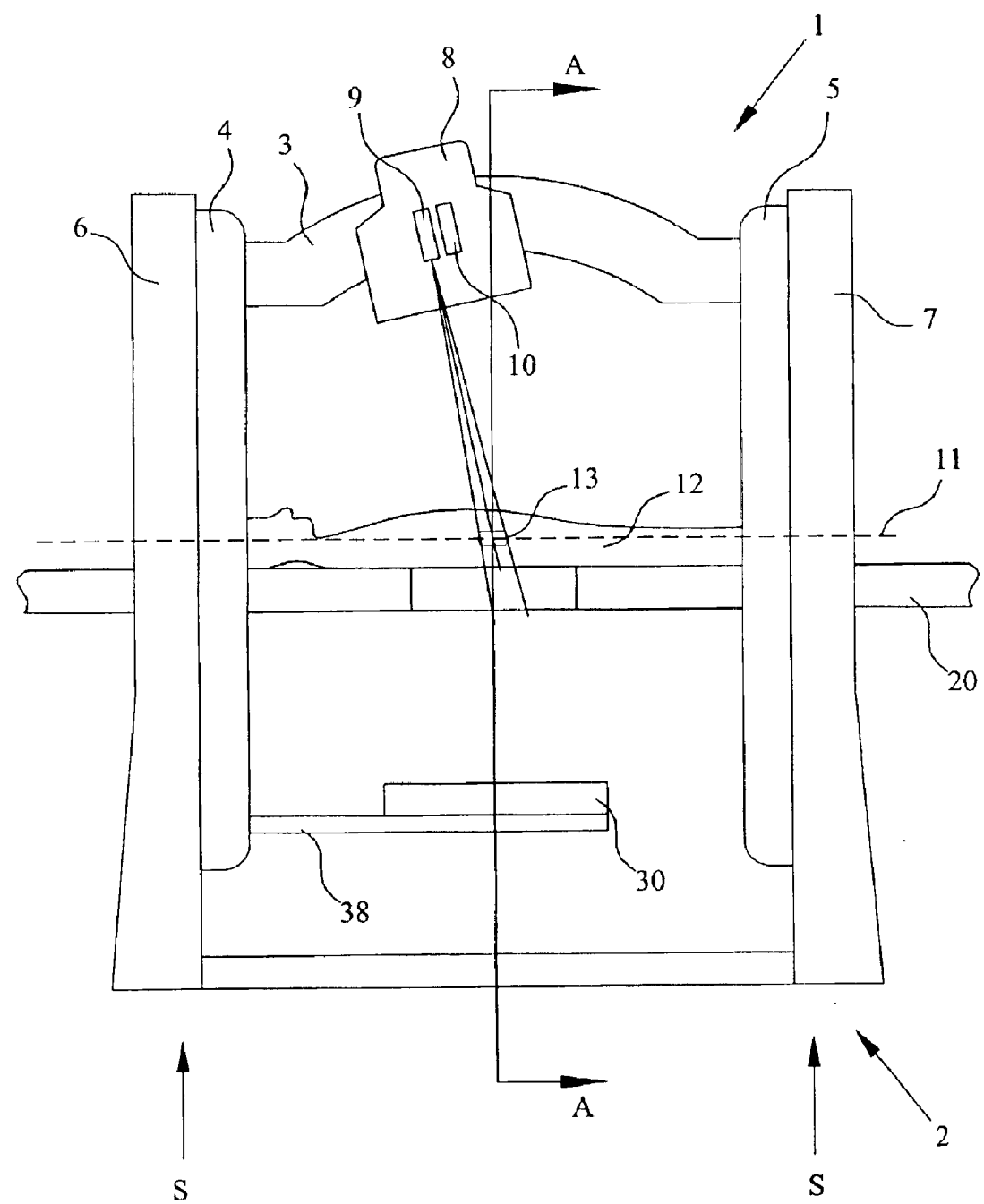
FIG. 2 is a sectional view of a first embodiment of a radiation machine according to the present invention delivering a treatment radiation dose to a patient.
Figure 3:
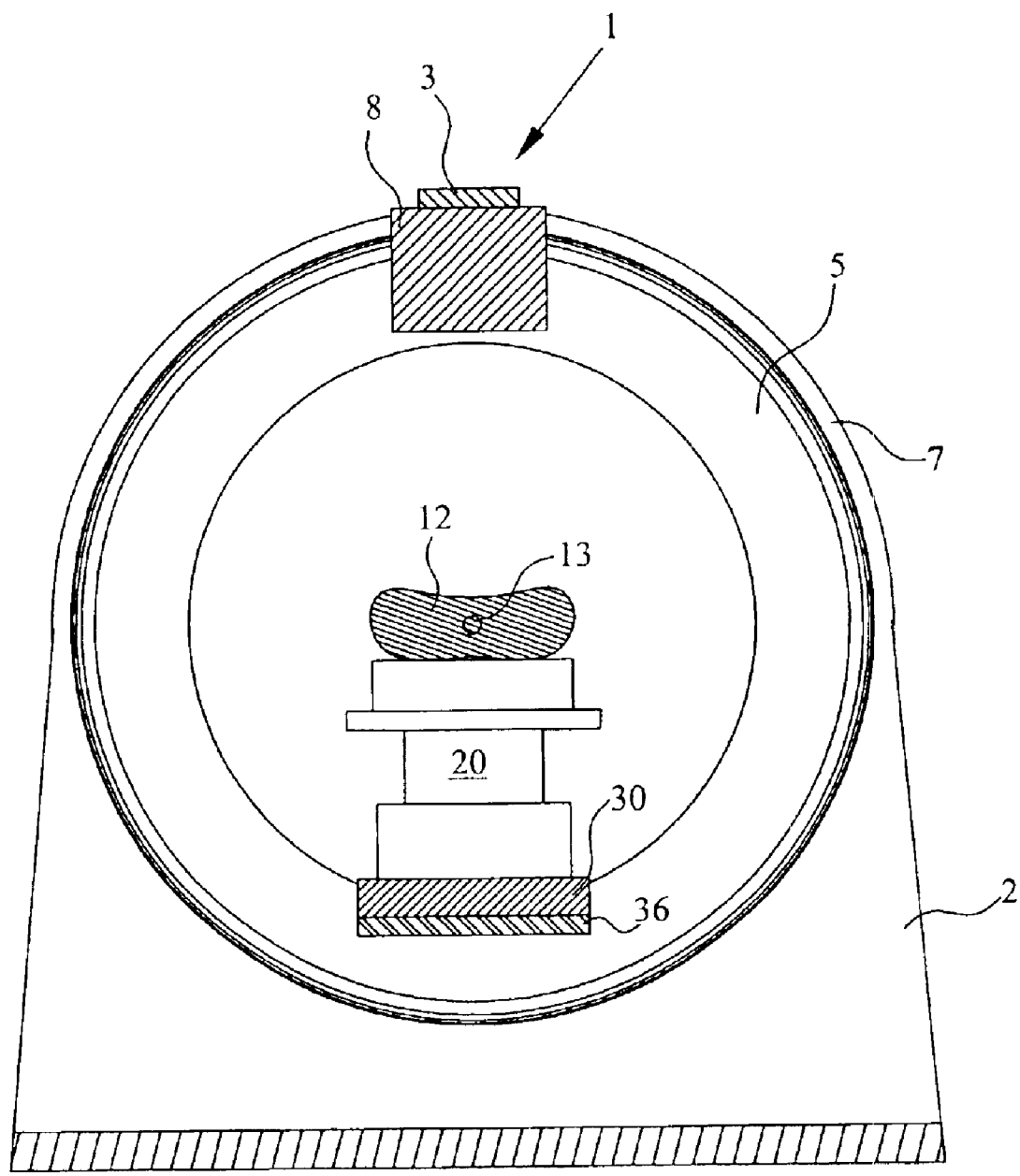
FIG. 3 is a sectional view of the embodiment illustrated in FIG. 2 taken along the line A—A.

In FIG. 2, a side view of a first embodiment of a radiation machine with an imaging system according to the invention is illustrated. FIG. 3 is the sectional view of this embodiment of FIG. 2 taken along the line A—A. A radiation head 8 is mechanically supported by an inner gantry part, generally denoted by 1. The inner gantry part 1 comprises in the present embodiment a circular arc portion 3, a first ring portion 4 and a second ring portion 5. The radiation head 8 is movable along the arc portion 3 from the first 4 to the second 5 ring portion. An object 12, preferably a human patient, is placed on a body-supporting couch 20, whereby a treatment radiation source 9 in the radiation head 8 is arranged to direct a treatment beam or dose package to a target volume 13 in the patient 12. In this embodiment, the ring portions 4, 5 of the inner gantry part 1 are situated on either side of the target volume 13. The ring portions 4, 5 are rotatably supported by an outer gantry part 2, comprising a first support portion 6 and a second support portion 7. In other words, the inner gantry part 1 is arranged with two supporting locations S with respect to the outer gantry part 2 on opposite sides of the treatment volume 13. Such a design, guarantees that the center of mass of the inner gantry part 1 always is situated between the support locations S and therefore a relative low bending moment is present in the gantry. This stable arrangement makes it possible to rotate the inner gantry part 1 relative the outer gantry part 2 around a substantially horizontal rotation axis 11 with a much faster rotation speed than recommended by the International Electromechanical Commission (IEC). Rotation speed below 20 s per revolution is easily obtained and a rotation speed below 10 s per revolution is routine. It is even possible to achieve a rotation speed of about, or sometimes even faster than, 6 s per revolution, without any major movement artifacts.

The treatment volume 13 is preferably positioned at the rotation axis 11. Thus, since the inner gantry part 1 is rotatable around the rotation axis 11, the treatment radiation source 9 may irradiate the treatment volume 13 from above, below and from either side thereof. In addition, the arc portion 3 and the movable radiation head 8 makes it possible to achieve a non-coplanar treatment. The center of curvature of the circle arc portion 3 is situated within the treatment volume 13, therefore the radiation head 8 with the treatment radiation source 9 maintains the radiation direction towards the treatment volume 13 even if the head 8 moves along the arc portion 3. By combing the movement of the head 8 along the arc 3 with the rotation of the inner gantry portion 1 around the patient 12, a multitude of irradiation directions is obtained.

The mechanical operation and support of the rotatable inner gantry part 1 is easily provided with e.g. conventional gear solutions and bearings. By also introducing sliding contacts between the inner 1 and outer 2 gantry part, preferably in connection with the mechanical bearing, a true continuous rotational motion may be achieved.

Figure 4:
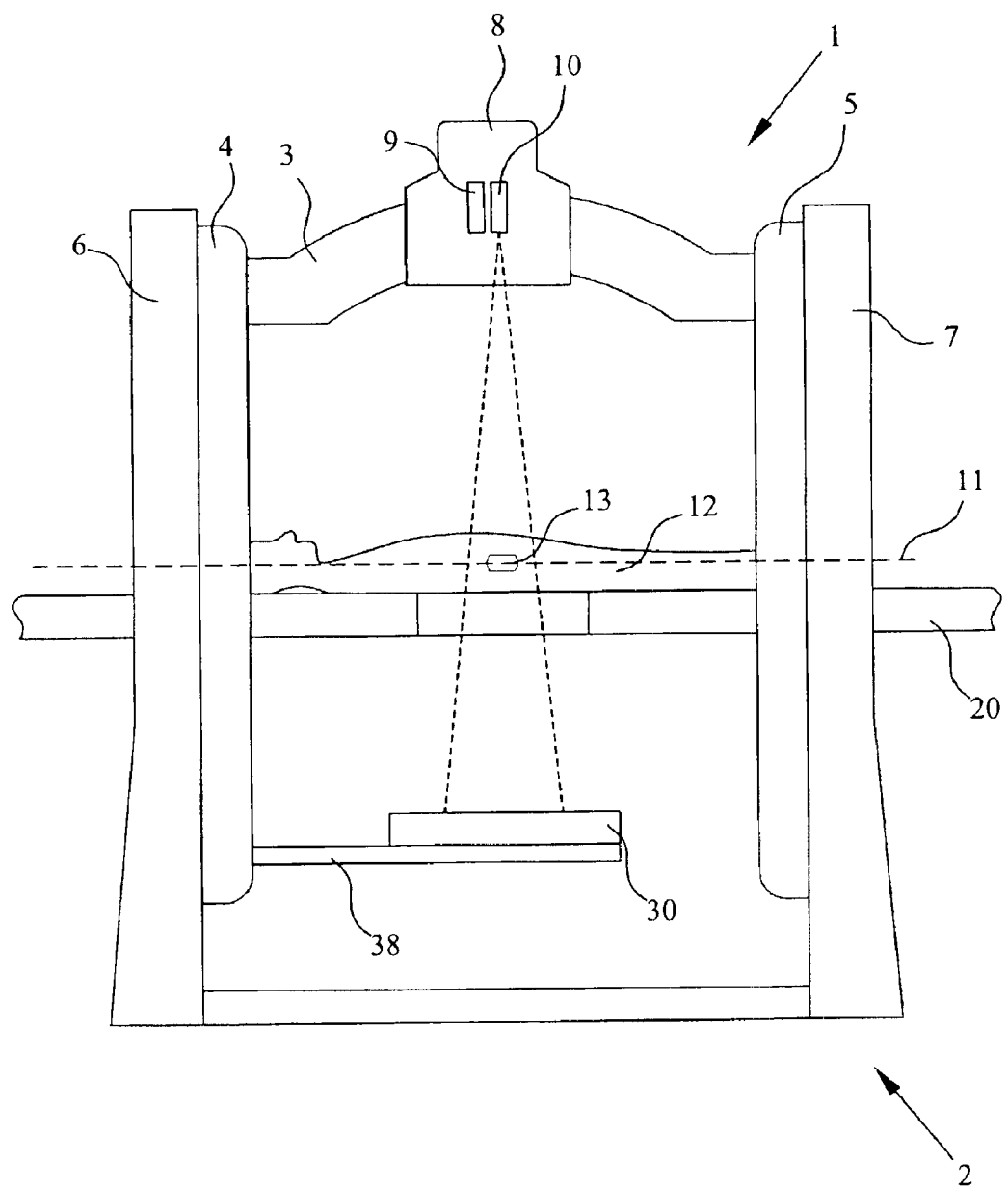
FIG. 4 is a schematic drawing of the radiation machine of FIG. 2 recording an image of the patient.

In the radiation machine, an imaging system is provided, comprising a diagnostic radiation source 10 and a detector 30. The diagnostic radiation source 10 is arranged in the inner gantry part 1, preferably in the radiation head 8 together with the treatment radiation source 9 or on one of the outside surfaces of the radiation head 8. However, other placements of the diagnostic radiation source 10 are possible, e.g. on either ring portion 4, 5 or in a separate radiation head (not illustrated) also arranged on the circle arc portion 3. The diagnostic radiation source may irradiate the patient 12 with a diagnostic radiation beam as in FIG. 4. The beam passes through the patient 12, preferably in the part of the patient including the target volume 13, and is detected by the detector 30, supported on the inner gantry part 1 by an attachment means 38. Based on the detected beam, a processing means, e.g. a computer (not illustrated), provides an image of the patient, preferably illustrating the part thereof including the tumor and target volume. By rotating the inner gantry part 1 around the rotation axis 11 and continuously or intermittently irradiate the patient 12 with the diagnostic radiation beam, images from several different directions around the target volume 13 can be taken. From these images, a 3-dimensional representation of the patient with the tumor and adjacent tissues, organs and bones may be obtained, depending on the imaging technique of the diagnostic imaging system.

A preferred imaging technique used by the imaging system is computed tomography (CT). In CT imaging, the diagnostic radiation source consists of an X-ray tube producing a diagnostic radiation beam in form of photons with an energy range of keV. As the diagnostic radiation source and detector are rotated around the patient the detector register 1-dimensional projections of the patient. From these projections a 2-dimensional slice can be reconstructed by the processing means. Each revolution of the inner gantry provides one such slice. By moving the radiation head and therefore the diagnostic radiation source along the arc portion for each revolution and/or moving the body-supporting couch along the rotation axis, a series of slices may be obtained. From this series of 2-dimensional slices, a 3-dimensional image of the portion of the patient irradiated with the diagnostic radiation beam is reconstructed. This gives a high quality, high-resolution image of the internal tissues, organs and structures, possible also the tumor itself, of the patient. From this image, relevant information, including location of reference points, size, shape and position of tumor relative the reference points may be identified.

A more preferred imaging technique is a development of the conventional CT imaging, namely cone-beam computed tomography. Mechanical operation of a cone-beam CT imaging system is similar to that of a conventional CT imaging system, with the exception that an entire volumetric image is acquired through a single rotation of the diagnostic radiation source (X-ray tube) and detector around the patient. In each recording, a 2-dimensional projection of the patient is obtained. By changing the recording angle, i.e. rotate the inner gantry, several such 2-dimensional projections at different angles are provided. The processing means uses adapted software and mathematical algorithms to reconstruct a 3-dimensional image of the patient from the projections. In other words, with cone-beam CT imaging, a single rotation of the radiation source and detector provides all information necessary to produce the patient image, whereas conventional CT imaging requires several such rotations to obtain the same information. In addition, the cone-beam CT imaging has some further advantages over conventional CT imaging, including largely isotropic spatial resolution and flexibility in the imaging geometry.

Cone-beam CT imaging together with the stable and fast rotating gantry of a radiation machine according to the invention, may provide a 3-dimensional image of the patient from a rotation of 6 s. This should be compared to the prior art radiation machines with imaging systems, which have a rotation speed of about 1 min per revolution, during which the patient may move considerable. The fast rotation speed according to the invention makes it possible to get images with a very high accuracy and resolution, since the patient may lie relatively still during this short time of 6 s.

Although, the diagnostic imaging system have been described as a (conventional or cone-beam) CT system, other imaging systems may also be applied according to the present invention.

Returning to FIG. 4, the detector 30 of the imaging system is preferably arranged diametrically across the radiation head 8, on the opposite side of the patient 12 to the diagnostic radiation source 10. The detector 30 should be attached to the inner gantry part 1, in order to rotate together with the radiation source 10 around the rotation axis 11. An attachment means 38 as in FIG. 4, which attaches the detector 30 to one of the ring portions 4 may be used. Preferably, this attachment means 38 is turnable or pivotal so the detector 30 may be moved out from the radiation machine to allow easy access and exchange. The sliding contacts between the inner 1 and outer 2 gantry part provides continues connection between the detector 30 and the image processing means (not illustrated).

Figure 5:
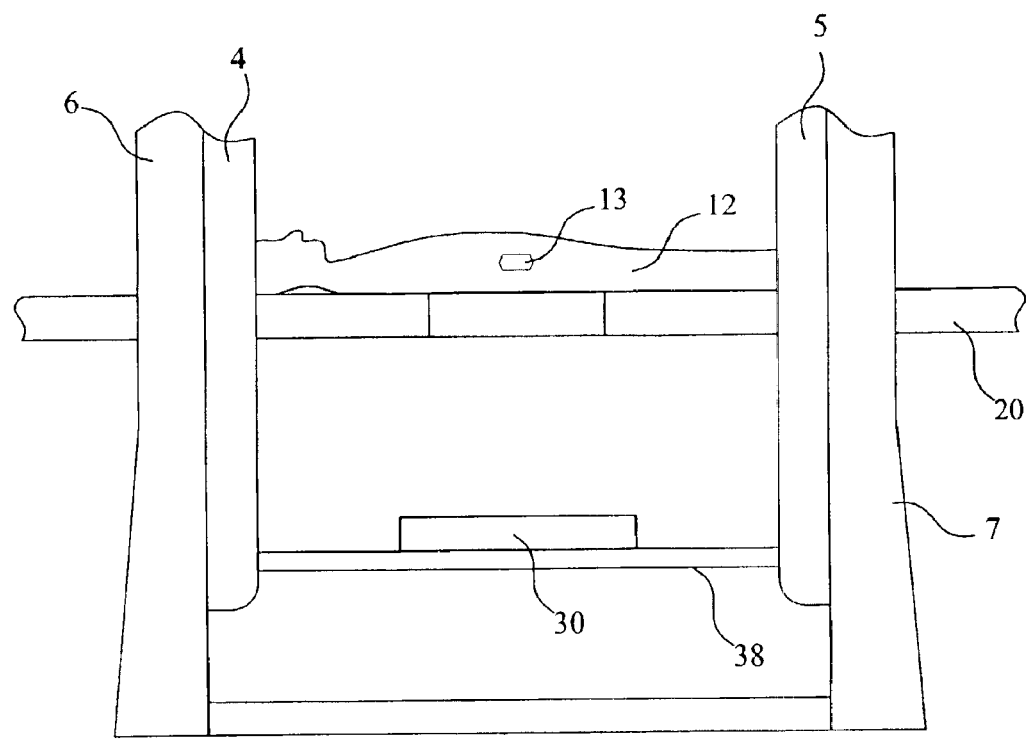
FIG. 5 is a drawing illustrating a second embodiment of a detector attachment applicable with present invention.

A more stable attachment means 38 is illustrated in FIG. 5, where the attachment means 38 is connected to both ring portions 4 and 5. This stable design makes it possible to use even faster rotation speeds without obtaining any movement artifacts of the detector 30.

Figure 6:
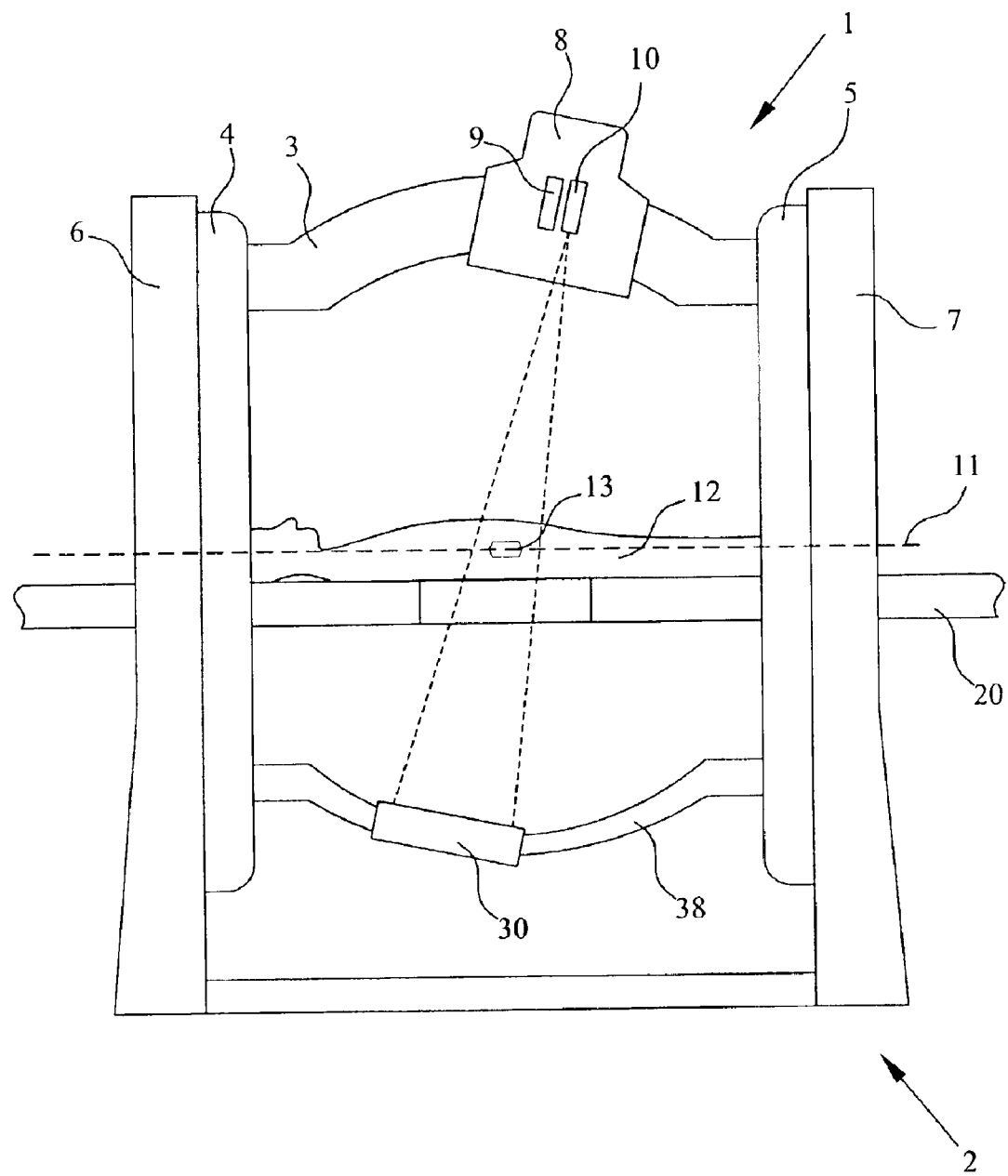
FIG. 6 is a drawing illustrating a yet another embodiment of a detector attachment applicable with present invention.

In another embodiment in FIG. 6, the attachment means 38 is in the form of a circle arc, similar to the circle arc portion 3, onto which the radiation head 8 is movable. With such an arrangement, the detector 30 may be moved along the attachment means 38, thereby always being on the opposite side of the treatment volume 13 in the patient 12 to the diagnostic radiation source 10. This arrangement also makes it possible to obtain non-coplanar CT imaging.

The detector of the present invention is preferably adapted for both the diagnostic imaging system and imaging with the treatment radiation. In other words, with a (conventional or cone-beam) CT imaging system, using low energy photons (in the order of keV), the detector should preferably be able to detect both the low energy diagnostic radiation and the high energy (in the order of MeV) treatment radiation. With such a design, the one and same detector may be used for both portal imaging, with the treatment radiation, and CT imaging, with the diagnostic radiation. This reduces both the cost and space required, since instead of using two detectors only one is arranged in the radiation system. The detector therefore, preferably, has a detectable range of photons with energies between 1 keV to 100 MeV. Such a detector 30 is illustrated in FIG. 7 together with a processing means 40 according to the present invention.

Figure 7:
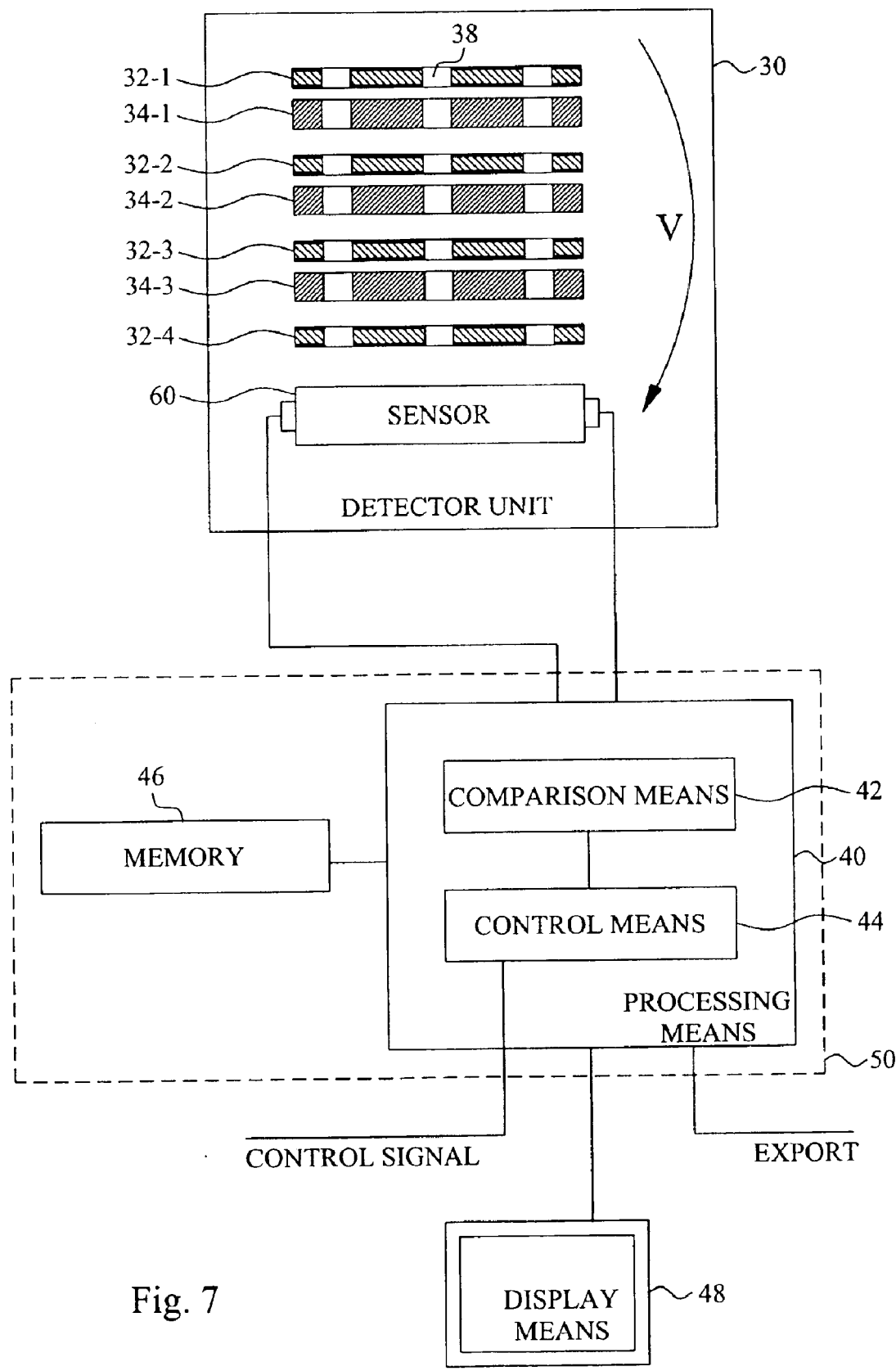
FIG. 7 illustrates a portion of the diagnostic imaging system according to the present invention.

The detector design 30 in FIG. 7 comprises a preamplification unit in form of a stack of alternating amplifiers 32-1 to 32-4 and converters 34-1 to 34-3 and a sensor 60. The preamplification unit and sensor 60 are located in a housing containing a gas. Suitable gases include Xe, Ar, Kr and Ne, but also gas mixtures are conceivable, including gas mixtures with quenching gases. The gas or gas mixture may or may not be pressurized, or it could be provided at sub-atmospheric pressure, according to the art. The top cover of the housing is preferably thin and light to maximize the number of low energy photons reaching the gas volume. A thin metal foil of e.g. Al or different polymers, including MYLAR®, could be used.

The converters 34-1 to 34-3 preferably comprises a perforated sheet of a material having the ability to convert incident photons into electrons through electromagnetic interactions, e.g. via Compton effect, pair-production and/or photo electric effect. The converters 34-1 to 34-3 are e.g. made of heavy metal with a thickness of preferably 0,1 to 1 mm. The converters 34-1 to 34-3 may also be progressively thicker towards the bottom of the stack compared to the top converters to match the higher occurrence of lower energy photons in the top layers relative to the bottom layers.

The amplifiers 32-1 to 32-4 consists in a first embodiment of a thin insulting meshed foil, e.g. of Kapton®, which is metal-clad on both sides and perforated by a regular matrix of holes 38. Suitable dimensions of the amplifiers 32-1 to 32-4 may be a thickness of the insulating foil of 50 $\mu$m, of the metal claddings of 5 $\mu$m. If a potential difference, schematically illustrated as V in the figure, is applied across the insulator/between the metal claddings a dipole field will develop in the holes 38.

Incident (treatment or diagnostic) radiation will ionize the gas in the housing, which will dissociate into electrons and corresponding positively charged ions. The electrons released from the gas will drift towards the high field through the holes 38 in the amplifiers 32-1 to 32-4 and become focussed therein. The focussed electrons will then interact with atoms or molecules of the gas thereby causing ionization thereof to produce a plurality of electrons (and positive ions). Thus, the high electric field regions will lead to an avalanche multiplication of electrons, which then may be detected by the sensor 60. Electrons are also released, as was discussed in the foregoing, when incident photons hit the converters 34-1 to 34-3, which contribute to the avalanche effect.

By using the stack with amplifiers 32-1 to 32-4 and converters 34-1 to 34-3 by turn, it is possible to detect both high and low energy incident radiation (photons). The high energy photons penetrates far into the stack structure before being converted into electrons, whereas low energy photons convert into electrons already in the uppermost converter 34-1 or even in the gas layer between the housing and the first amplifier 32-1.

Figure 8:
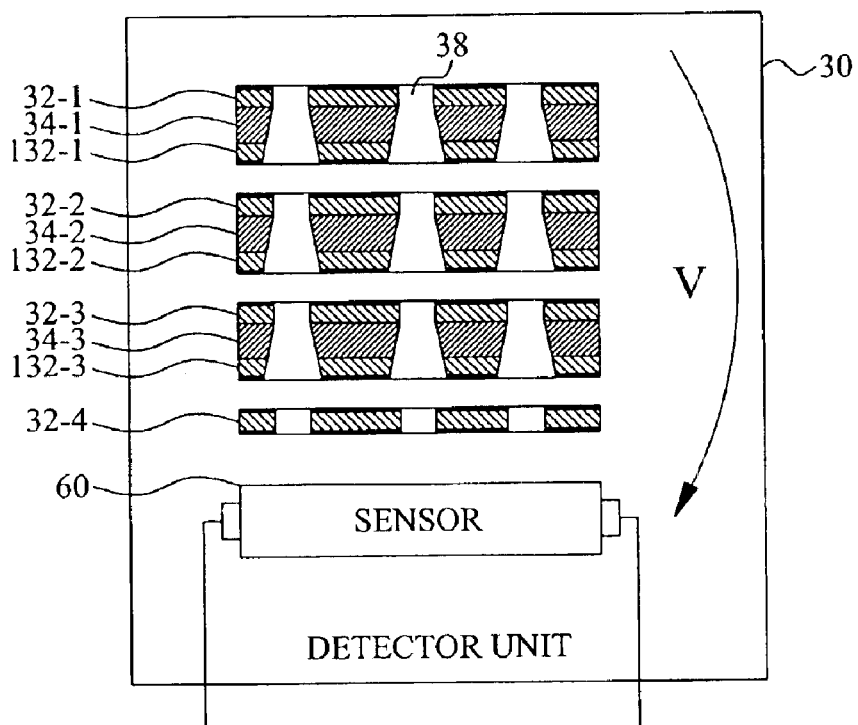
FIG. 8 is a second embodiment of a detector design applicable with the present invention.

Another embodiment of a detector 30 according to the invention is illustrated in FIG. 8. In this embodiment the preamplification unit of the detector 30 comprises a stack of amplifiers 32-1 to 32-4, converters 34-1 to 34-3 and guiding layers 132-1 to 132-3 arranged onto each other as in FIG. 8. The amplifiers 32-1 to 32-4 are similar to the corresponding ones in FIG. 7, i.e. comprising a metal layer deposited on an insulating material. Underneath the insulating layer, a converter 34-1 to 34-3 is arranged in form of a thick metal layer. This layer is preferably at least one order of magnitude thicker than the metal foil of the amplifiers 32-1 to 32-4. Below the metal layer of the converters 34-1 to 34-3, a guiding insulating layer 132-1 to 132-3 is provided, on which a second bottom metal foil is deposited. This composite amplifier-converter-guiding structures is perforated by a matrix of holes 38, with a general cone shape, i.e. a smaller 'entrance opening' than 'exit opening' when going from the top of the detector 30 towards the sensor 60.

A problem with the detector embodiment of FIG. 7, is that electrons passing through the holes 38 in the converters 34-1 to 34-3 diffuses into the metal layer of the converters 34-1 to 34-3. However, the composite structure of FIG. 8 solves this electron diffusion problem, and thereby increases the efficiency of the detector 30.

Figure 9:
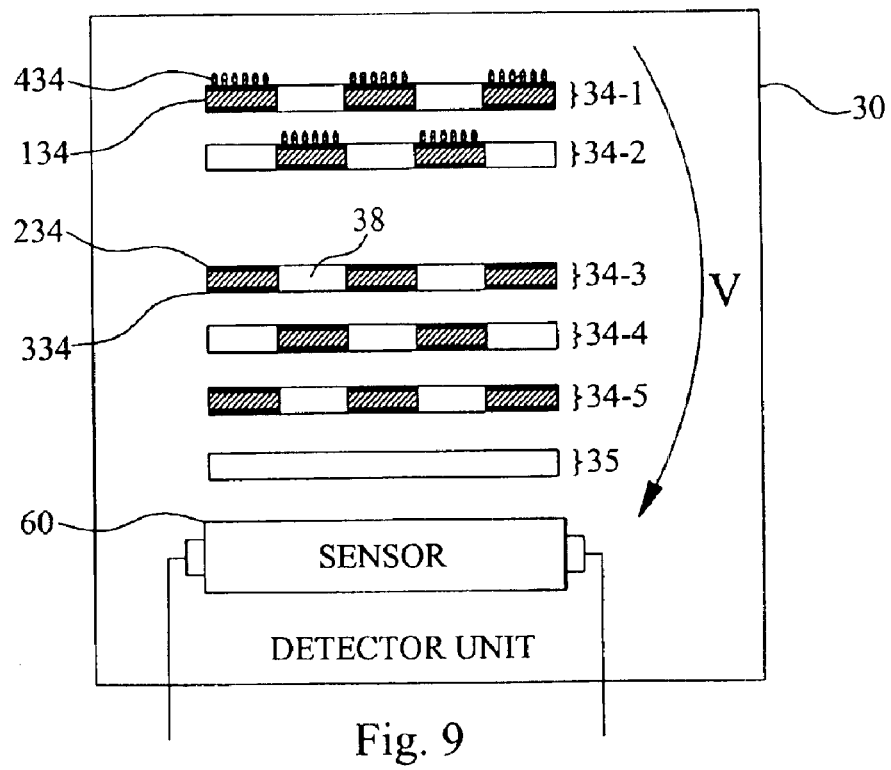
FIG. 9 is yet another embodiment of a detector design applicable with the present invention.

A preferred embodiment of a detector 30 used in connection with a radiation therapy machine according to the present invention is schematically illustrated in FIG. 9. Instead of comprising alternating amplification and conversion layers, as in FIGS. 7 and 8, this detector design comprises a stack of converters 34-1 to 34-5. Each converter 34-1 to 34-5 has a central supporting layer 134, normally of an insulating material. On each side of the supporting layer 134, an electrode layer 234, 334 is arranged. These electrode layers 234, 334 may be a simple metallization on both sides of the insulating material 134.

In order to increase the probability of electromagnetic interaction of the incident radiation beam, i.e. formation of free electrons, a columnar structure 434 with multiple columns may be arranged extending from all or some of the converters 34-1, 34-2. The columns provide a large number of surface crossings of the incident radiation on its path through the structure. This results in efficient conversion of the incident radiation into electrons, and may also give a slight electron multiplication effect as an inherent property of the columnar structure 434. Preferably, the columnar structure 434 is formed as a cesium iodide (CsI) layer, which is deposited on the converter 34-1, 34-2 at a suitable location.

Through the converters 34-1 to 34-5, holes 38 are provided, as in the detectors of FIGS. 7 and 8. However, in contrary to the detector designs discussed in connection to FIGS. 7 and 8, in the present detector 30, the holes of one converter is staggered with respect to holes of other converters. The effective conversion area will be increased and the probability of incoming radiation passing through the stack without interaction with the converters 34-1 to 34-5 will be significantly reduced and a more efficient detector 30 is accomplished.

The actual design of the stacked detector layer structure in FIG. 9 ease the requirements of applying a relative high potential difference V over the layers, typically in the order of kV, across the stacked structure. This high potential is in most cases required for the detector embodiments of FIGS. 7 and 8 to obtain an avalanche multiplication of electrons to be detected by the sensor 60. The required potential difference for the efficient detector in FIG. 9 is about ten orders of magnitude lower than for the two other embodiments discussed above.

However, in order to increase the spatial resolution of the detector, it is beneficial to use a suitable multiplication structure 35, preferably arranged just above the sensor 60, for avalanche multiplication of electrons to be detected by the sensor 60.

For electron multiplication, any conventional multiplier such as a parallel plate chamber, a multiwire proportional chamber or a gas electron multiplier, may be used.

The converter(s) used in the detectors may be provided with diamond (uniformly or non-uniformly) for improving the conversion efficiency of incoming radiation (especially applicable to X-rays) into electrons. Preferably, CVD (Chemical Vapor Deposition) techniques are used for causing diamond deposition, for example vaporized from methane ($CH_4$) gas. CVD is generally a gas-phase chemical reaction occurring above a solid surface, causing deposition onto the surface. CVD techniques for producing diamond normally require some means of activating gas-phase carbon-containing precursor molecules, for example by maintaining the substrate within a given temperature interval and ensuring that the precursor gas is diluted in an excess of hydrogen.

In the converter(s), CVD diamond may be used as insulating material, for example sandwiched between two electrode layers. For manufacturing, the CVD diamond may be deposited onto a first metal electrode layer, with a vacuum evaporated second metal layer on top of the CVD diamond. Alternatively, it is possible to provide the CVD diamond as a diamond film or coating on one or both of the electrodes and/or on the walls defining the capillary holes. The use of CVD diamond is expected to give a very high yield (~20) of secondary electrons, thus resulting in a very efficient converter structure.

Returning to FIG. 7, at the bottom of the detector 30 a sensor 60 is arranged to collect the converted electrons. The sensor 60 may be e.g. a Multi-Wire Proportional Chamber (MWPC), a Micro Strip Gas Chamber (MSGC), a circuit board, e.g. Printed Circuit Board (PCB), a Charged Coupled Device (CCD) or another charge collecting means together with appropriate read-out electronics to provide data to the processing means 40. An example of a sensor design 60 is a circuit board comprising layers of an insulator, between which there are metal conductors provided. Each conductor is connected to one charge collection pad. The pads are made of metals, preferably Cu, Au or Al and made using conventional photolithographic techniques known in the art. The pads are preferably distributed to correspond to the geometry of holes 38 in the converters 34-1 to 34-3 and amplifiers 32-1 to 32-4. Each pad then has its own connection to the read-out electronics, e.g. in form of an ASIC (Application Specific Integrated Circuit).

Figure 10:
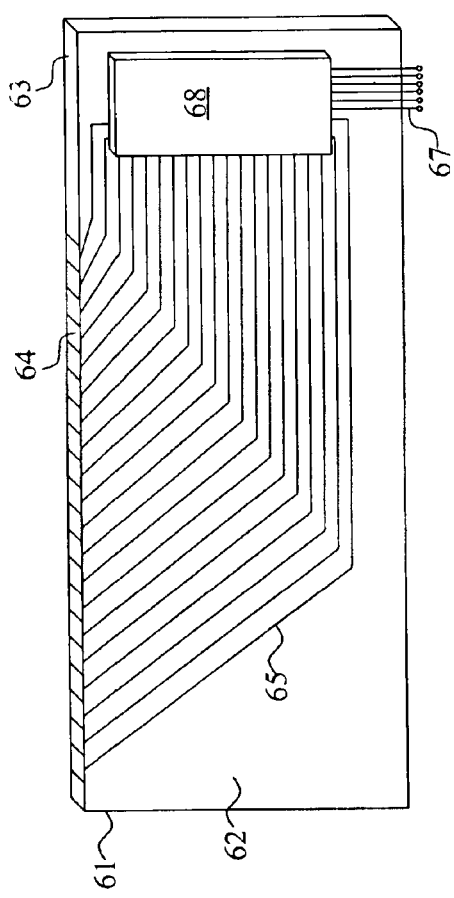
FIG. 10 illustrates a circuit board to be used in an embodiment of a sensor in a detector applicable with the present invention.

A preferred embodiment of a circuit board 61 is illustrated in FIG. 10. The circuit board 61 is defined by two main surfaces 62 and four edge surfaces 63. A row of radiation sensitive elements 64 is arranged at one of the edge surfaces. Typically, connection lines 65 lead from each radiation sensitive element 64 to signal processing means 68, such as an ASIC, preferably without any wire-crossings. The signal processing means 68 is preferably located at the same board 61 as addressed radiation sensitive elements 64 but at a distance therefrom to avoid radiation damages on the sensitive electronics. Read-out connections 67 are provided at the signal processing means 68 to connect the circuit board 61 to external processing means. Thus, with the circuit board design of FIG. 10, a small surface at the edge portion of the circuit board 61 is used as an area for radiation sensing, whereas the larger main surface 62 is used for the space-demanding wiring and electronics.

Figure 11:
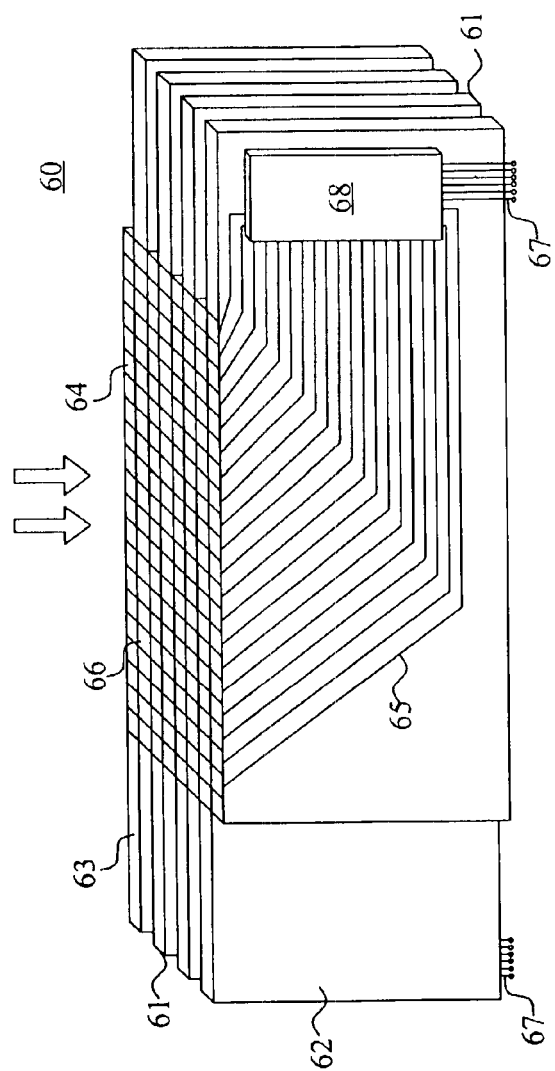
FIG. 11 is a preferred embodiment of a sensor used in a detector applicable with the present invention.

By arranging a number of circuit boards 61 of FIG. 10 adjacent to each other, a radiation sensor 60 is obtained, as is illustrated in FIG. 11. The boards 61 are preferably placed in a support structure (not illustrated), facilitating removal/insertion of individual boards 61. The boards could also be adhesively attached to each other, e.g. by means of glue, or still differently arranged. In such a way, a sensor surface 66 is formed by the rows of radiation sensitive elements 64. The signal processing means 68 generally protrudes above the main surface 62 of each circuit board 61 and is in a preferred embodiment placed at an end portion of the respective circuit board 61. By arranging the circuit boards 61 such that adjacent boards have their signal processing means 68 at opposite ends, as illustrated in FIG. 11, and restricting the maximum allowed protrusion of the signal processing means 68 to one circuit board thickness, a compact sensor 60 is formed. Another embodiment achieves a similar advantageous space utilization by arranging the signal processing means of adjacent boards in a non-overlapping way at different heights, instead of at different board ends. The area of the formed sensor surface 66 is preferably in the order of $dm^3$, with the total number of sensitive elements in the order of hundred thousand.

The radiation sensitive elements 64 may be charge collectors, radiation sensitive diodes, e.g. photodiodes, or any other element capable of sensing the radiation reaching the sensor surface. Incident electrons are preferably sensed by pixels made of thin film of a conducting material, e.g. copper. The copper islands can reside charge of the surrounding radiation, which may be collected via the signal processing means 68 at predefined points of time.

The main body of the circuit board 61, is preferably composed of a non-conducting material, such as a polymer material. The connection lines 65 between the individual radiation sensitive elements 64 and signal processing means

68 are for example realized as metal wires. It is desirable to implement a line pattern that uses the main surface 62 of the board 61 as efficiently as possible, preferably without unnecessary crossings.

It should be understood that other geometrical structures of the circuit boards may be used. Anyhow, each circuit board is defined by two main surfaces and at least one edge surface, where the area of the edge surface typically is substantially smaller than the area of the main surfaces.

The radiation sensitive elements arranged on the respective circuit board are preferably placed such that, in operation, the edge surface and an active surface of each of the radiation sensitive elements are facing the incident radiation. Advantageously, the radiation sensitive elements are arranged at or in the vicinity of at least one edge surface of the respective circuit board.

Other detector structures are also conceivable according to the present invention, including an amorphous silicon flat-panel detector, preferably adapted for both high and low energy radiation, i.e. treatment and diagnostic radiation, respectively.

Returning once more to FIG. 7, the processing means 40 reconstructs an image based on the data forwarded from the sensor 60 in the detector 30. The processing means 40 comprises or has access to software adapted for creating the image from the measured and detected radiation. This means that the processing means 40 preferably has access to software for imaging based both on detected low energy radiation of the imaging system and detected high energy from the treatment radiation source. If a cone-beam CT imaging is used, the processing means 40 preferably stores the data corresponding to each 2-dimensional representation of the patient in a memory 46, either arranged in the processing means 40 or connected thereto. Based on the 2-dimensional representations, a full 3-dimensional image of the patient is provided by means of the dedicated software. This image may then be stored in the memory 46, displayed on a screen or monitor 48 and/or exported in a suitable format to a computer or similar means.

The determined image may also be compared to a reference image of the patient. This reference image could be the representation of the patient with the target volume, reference points and tumor tissue used in the treatment plan and/or an image determined in an earlier measurement and stored in the memory 46. The two images may then be displayed together on the screen 48 to manually compare the images. In such a comparison, changes in the position of the target volume/tumor may be detected, but also changes in the shape and size of the tumor. Based on this comparison and any found differences between the images, the medical personnel may update the treatment plane and the settings of the radiation machine, e.g. irradiation directions, treatment radiation dose, etc., accordingly. Thus, using the obtained image it is possible to detect if the patient has been misplaced during a just conducted radiation treatment. Reference points, the position of which is connected to the target volume, or the tumor tissue may be identified and their positions relative the desired and expected positions in the treatment plan can be determined. A subsequent treatment occasion is then adapted based on any misplacement to correct for the incorrectly performed preceding treatment. Also subsequent treatment may be adapted based on changes in the tumor itself, such as a decreased size and changed position due to lost of weight. The treatment plan is then updated accordingly.

These manually performed changes, corrections and adaptations probably are performed between two treatment occasions. However, the image information from the diagnostic imaging system in the radiation machine may also be used to automatically adapt and correct the ongoing treatment.

In the processing means 40, a comparison means 42 may be configured. This means 42 compares the determined patient image with a reference image, i.e. the corresponding image in the treatment plane and/or an earlier determined image. Using image-processing algorithms known in the art, the comparison means detects 42 any major or significant differences between the image and the reference. If a difference is detected, e.g. a misplacement of patient or change in tumor size or shape, a signal is input to a control means 44 arranged in the processing means. Based on the input signal, the control means 44 determines a control signal that corrects for the change. This control signal may be sent to the body-supporting couch and/or radiation head to e.g. change the position of the patient and adapt the treatment radiation, respectively.

The processing means 40 may be implemented as software, hardware, or a combination thereof. A computer program product implementing the processing means 40 or a part thereof comprises software or a computer program run on a general purpose or specially adapted computer, processor or microprocessor 50. The program may be stored in whole or part, on or in one or more suitable computer readable media or data storage means such as magnetic disks, CD-ROMs or DVD disks, hard disks, magneto-optical memory storage means, in RAM or volatile memory, in ROM or flash memory, as firmware, or on a data server. The processing means 40 may be implemented in a remote computer 50 connected to the radiation therapy machine, e.g. arranged in the monitoring room, where the medical personnel are during radiation treatment. A computer 50 arranged onto or in the vicinity of the radiation therapy machine may also implement the processing means 40.

Figure 12:
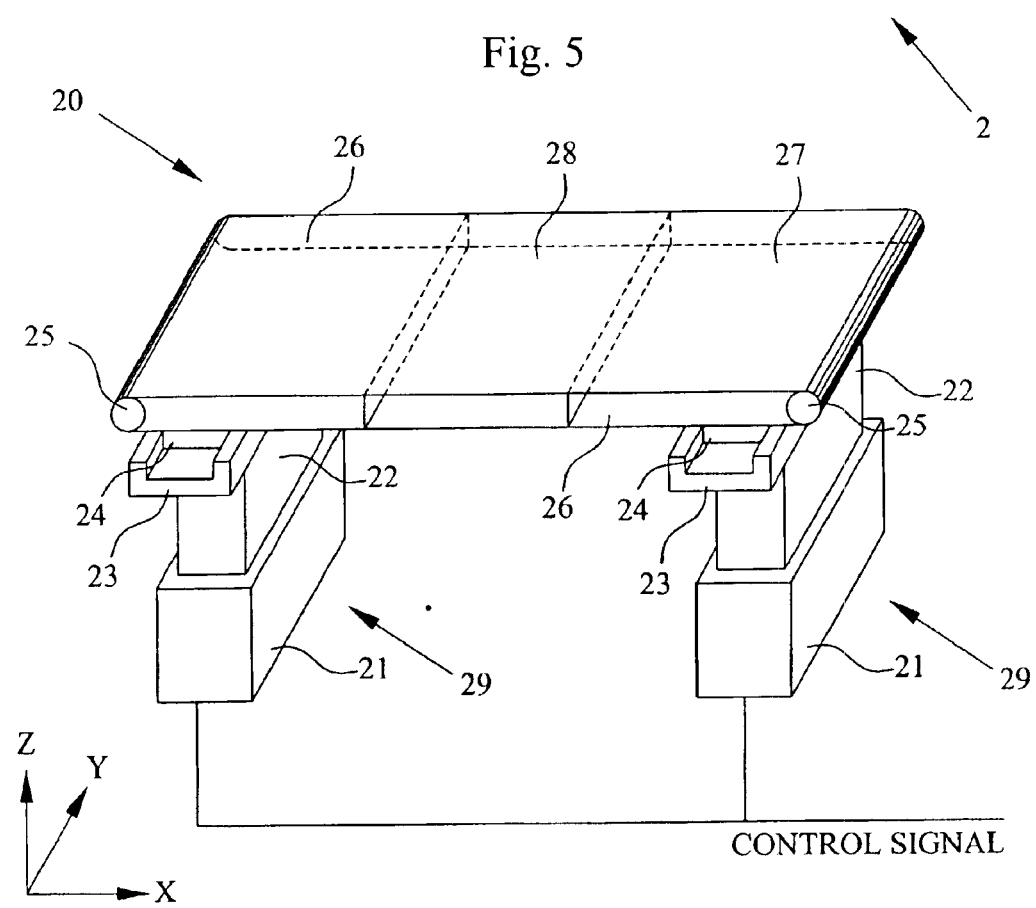
FIG. 12 is a perspective view of a couch that may be used in a radiation machine according to the present invention.

FIG. 12 illustrates a perspective view of an adjustable body-supporting couch 20 according to an embodiment of the present invention. The couch 20 comprises two couch support portions 29, which may be integrated in the gantry support or provided as separate means. From each support portion 29, a respective rigid couch support portion 26 extends towards the treatment volume in opposite directions. The front parts of the rigid couch portions 26 are placed apart from each other and thereby form an empty volume 28 therebetween. This empty volume 28, at operation of the radiation machine, is situated beneath the treatment volume. The rigid portions 26 are preferably interconnected by a thin foil 27 of a material with a low radiation cross section. The foil 27 may be provided as an endless belt, which is driven by two rolls 25 and thus serve for changing the position of the body along the rotation axis of the radiation machine.

The rigid couch portions 26 are preferably movable relative the gantry. This displacement is possible in at least two translation directions, vertically and horizontally. In FIG. 12 these directions are denoted y and z, whereas the movement of the belt-like foil 27 is along the x-axis. The motion along the y-axis is in the present embodiment accomplished by letting a protrusion 24 of the rigid couch portions 26 slide in a dedicated slot portion 23. The z-motion is accomplished by a piston 22 of the couch supports 29, which can be moved up and down in a cylinder 21.

In the couch supports 29, or in the vicinity thereof, adjusting means, preferably motor driven means (not illustrated), is arranged. This adjusting means can change the position of the couch in the x-, y- and/or z-direction based on a control signal. This signal may be the control signal form control means 44 in FIG. 7.

Instead of, or as a complement to, adjusting the position of the couch, the control signal form the control means 44 in FIG. 7 could be used to adjust the treatment radiation source. Such an adjustment, could be adjusting the position of the treatment radiation source relative the target volume by moving the radiation head along the arc portion of the inner gantry. In addition, the radiation dose may be adapted based on the control signal to consider changes in the tumor size.

With the radiation machine according to the present invention, it is thus possible to irradiate the target volume with the treatment radiation source and then take an image of the tissues and organs corresponding to the target volume using the diagnostic radiation system and diagnostic radiation source. The image is compared to a reference image, e.g. in the treatment plan, and any differences in patient position and/or size, shape and relative position of the tumour between the images are used to correct the following treatment. This procedure can be completely or partly automatic, requiring little or no human intervention. In the prior art, the patient has to be moved from the radiation machine to a diagnostic machine and then back again to accomplish the same result. Therefore the present invention saves cost and streamlines the radiation therapy process.

Figure 13:
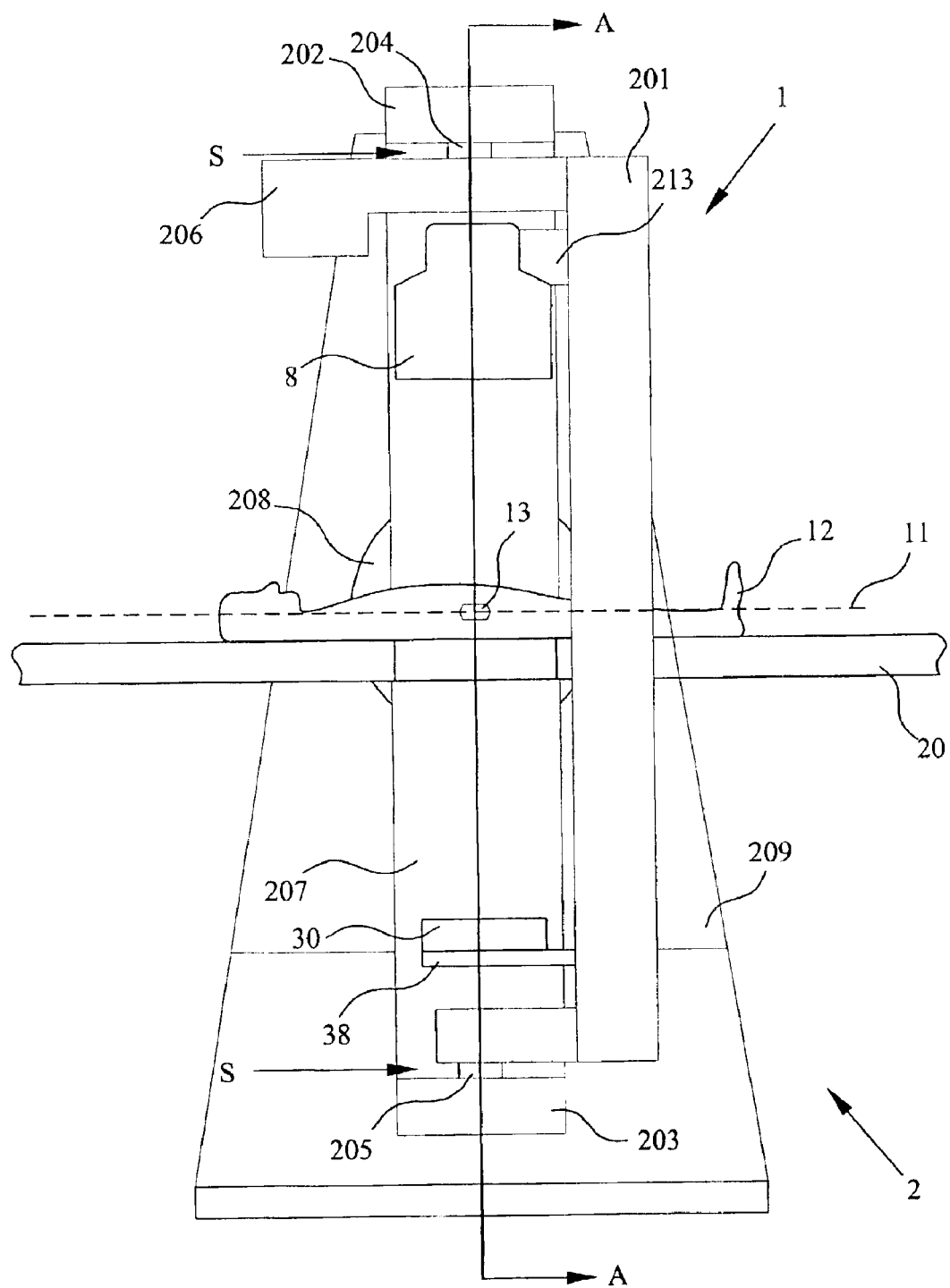
FIG. 13 is a side view of second embodiment of a radiation machine according to the present invention.
Figure 14:
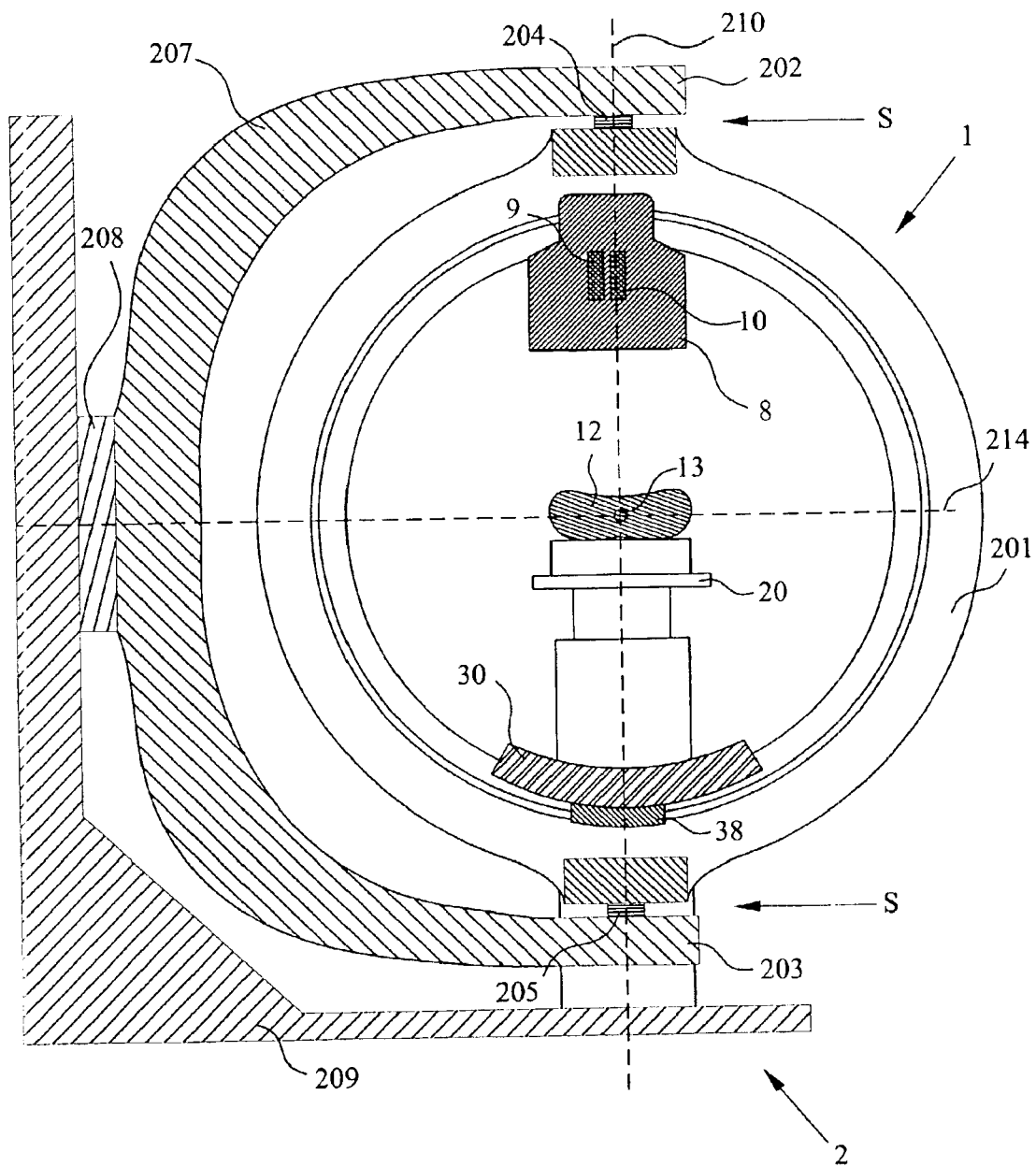
FIG. 14 is a sectional view of the embodiment illustrated in FIG. 13 taken along the line A—A.

In FIG. 13, a side view of another embodiment of a radiation machine with a diagnostic imaging system according to the present invention is illustrated. In FIG. 14, the radiation machine of FIG. 13 is illustrated in a sectional view along the line A—A in the axial direction. A radiation head 8, with a treatment radiation source 9 and preferably a diagnostic radiation source 10, is mechanically supported by an inner gantry part, denoted 1. In the present embodiment, the inner gantry part 1 comprises a head supporting arm 213, a ring portion 201 and a counter weight 206. In addition, a detector 30 is arranged through an attachment means 38 in the inner gantry part 1. The head supporting arm 213 and preferably the attachment means 38 are movable along the ring portion 201, which means that the radiation head 8 is able to rotate around a rotation axis 11. A patient 12 with a treatment volume 13 to be irradiated, is situated on a body-supporting couch 20, preferably positioned so that the target volume 13 is positioned at the rotation axis 11.

The inner gantry part 1 is supported by a first 204 and second 205 rotatable support of an outer gantry part 2. The outer gantry part includes a general C-shaped jaw portion 207, rotatably supported through a rotation connection 208 to a support portion 209. The first 204 and second 205 rotatable support are attached to front ends 202 and 203, respectively of the jaw portion 207. Thus, the inner gantry part 1 is provided with two support locations S with respect to the outer gantry part 2. These support locations S are situated on each side of the treatment volume 12, in a radial direction. The radiation head 8 with the treatment 9 and diagnostic 10 radiation source is rotatable around the rotation axis 11 and may thus irradiate the target volume 13 with the treatment radiation and take images thereof with the diagnostic radiation from all directions, including from below. In order to achieve non-coplanar treatment, the inner gantry part 1 is rotated either around a vertical rotation axis 210 by the rotatable supports 204, 205 or around a horizontal rotation axis 214 by the rotation connection 208.

In FIG. 13, it may be noticed that since the first 204 and second 205 rotatable supports are situated in the same plane as the radiation head 8 and the ring portion 201 is displaced from the vertical axis 210, the ring portion 201 applies a torque on the outer gantry part 2, which would tend to rotate the rotational connection 208. In order to compensate for this torque, a counterweight 206, is attached to the ring portion 201. This counterweight 206 is fixed to the ring portion and does no follow the rotation of the radiation head 8 and optional the detector 30.

As for the first embodiment of the radiation machine in FIG. 2, the embodiment of FIGS. 13 and 14 provides a very stable gantry, leading to a rotation speed of the radiation head and detector down to 6 s per revolution. Such a fast rotation, is well adapted for the diagnostic imaging system, since the patient can lie very still during this short rotation time, which in turn increases the accuracy and resolution of the obtained images.

Figure 15:
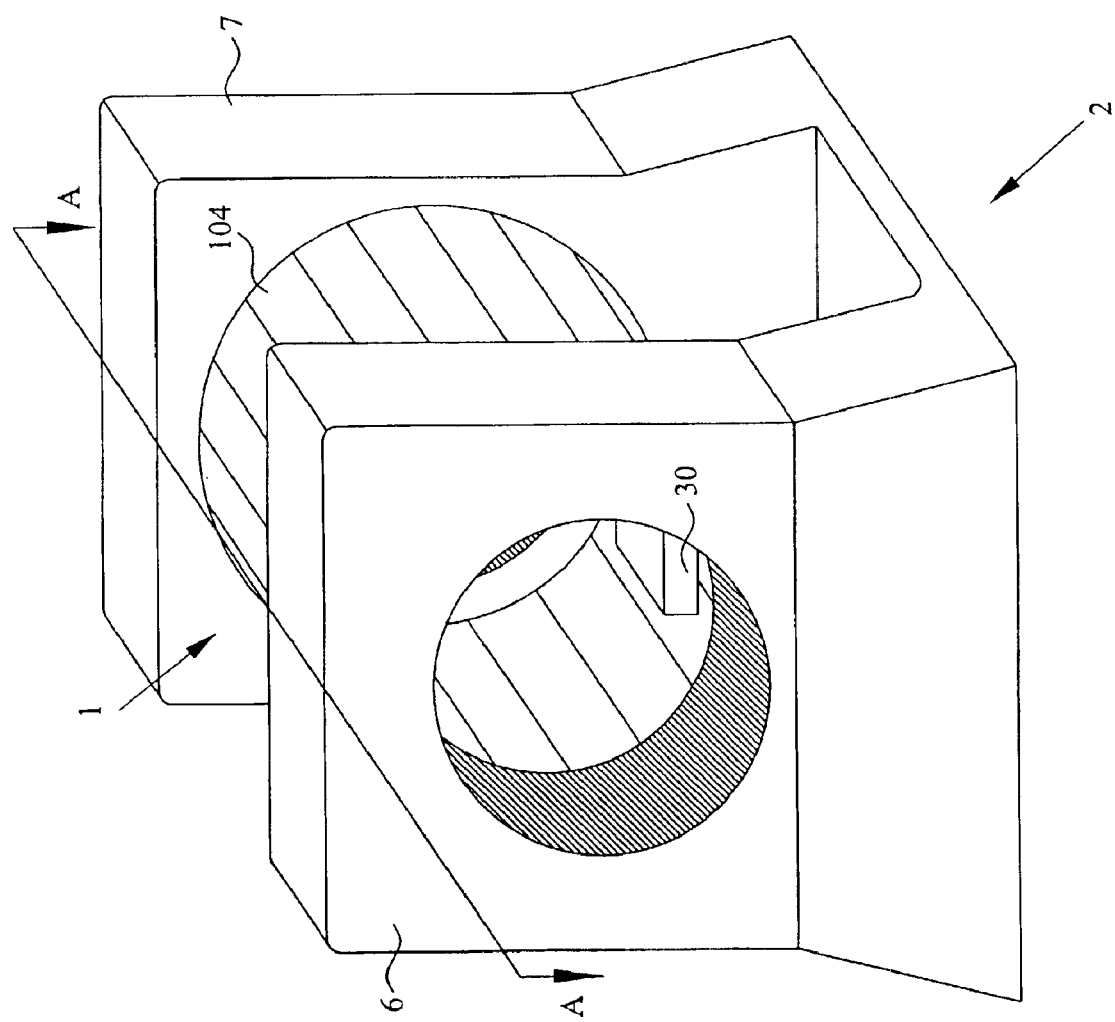
FIG. 15 is a schematic perspective view of yet another embodiment of a radiation machine according to the present invention.
Figure 16:
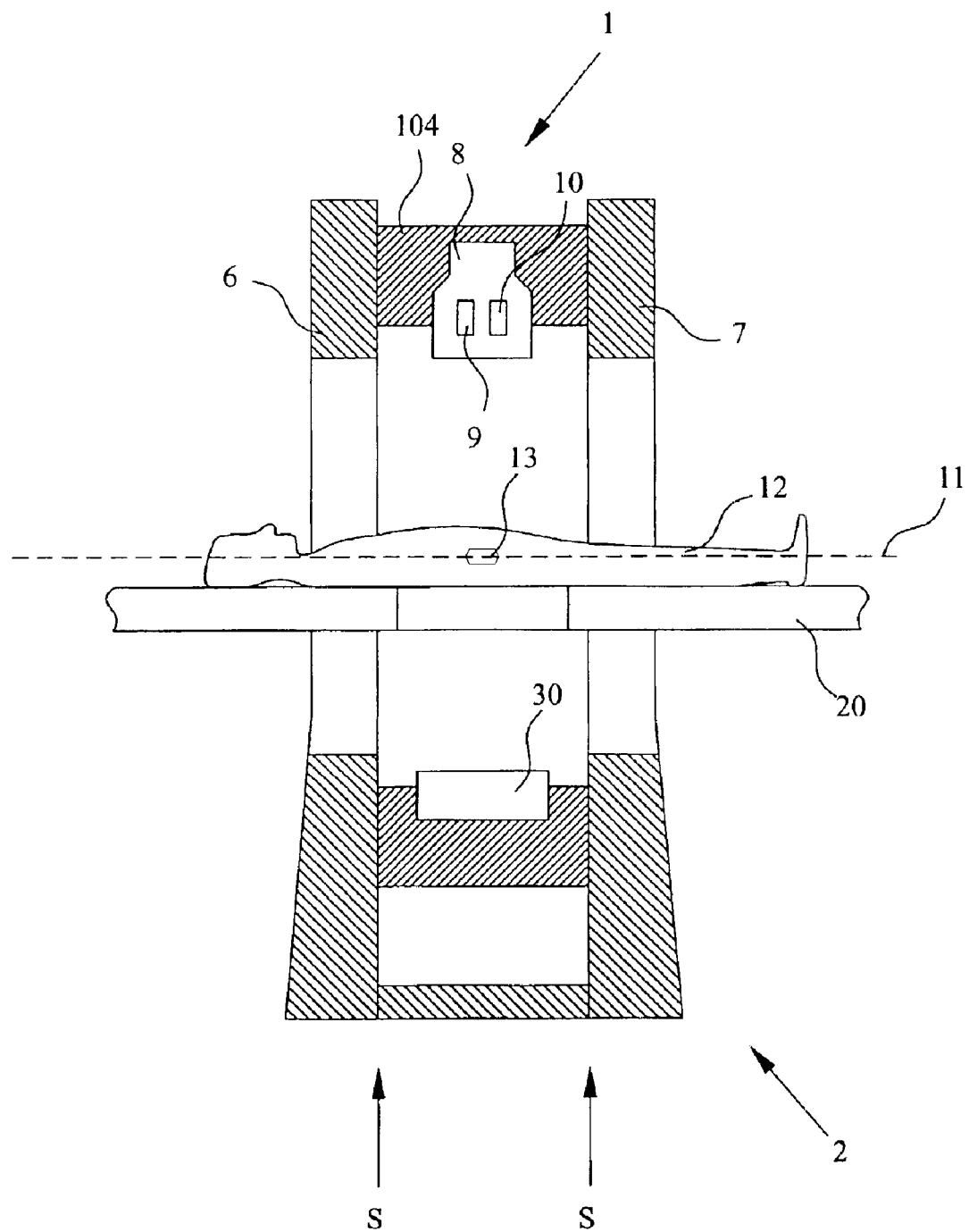
FIG. 16 is a sectional view of the embodiment in FIG. 15 taken along the line A—A with a patient arranged on a body-supporting couch.

Yet another embodiment of a radiation machine according to the present invention is illustrated in FIGS. 15 and 16. This embodiment is similar to the first embodiment discussed above in connection to FIGS. 2–6, except that the two inner ring portions 4, 5 in FIGS. 2–6 have been merged into a single ring portion 104. This ring portion 104 of an inner gantry part 1 is rotatably supported by a first and second support portion 6 and 7, respectively, of an outer gantry part 2. As is more clearly seen in the sectional view of the radiation machine in FIG. 16, taken along the line A—A in FIG. 15, the ring portion 104 is arranged with two supporting locations S with respect to the outer gantry part 2 on opposite sides of a treatment volume 13 in a patient 12. The patient 12 is in turn arranged on a body-supporting couch 20 passing through the inner and outer gantry parts 1 and 2, respectively. This stable arrangement makes a fast rotation possible without any major movement artifacts around a rotation axis 11, preferably situated in the treatment volume 13.

In the ring portion 104 a radiation head 8 with a treatment radiation source 9 and preferably a diagnostic radiation source 10 is provided. On the opposite side of the rotation axis 11, a detector 30 is arranged in the ring portion to detect diagnostic radiation from the diagnostic radiation source 10 passing through the patient 12. This detector 30 is preferably also adapted to detect high-energy radiation from the treatment radiation source 9 and may e.g. be realized as either of the detector designs in FIGS. 7–9.

The described embodiments of the radiation machine are merely given as examples of possible arrangements according to the present invention. The basic idea is that the radiation machine should have a very stable gantry, which is a requirement for high rotation speeds. This stable gantry design is accomplished by supporting the inner gantry part with the treatment and diagnostic radiation source and the detector by the outer gantry part at two support locations situated at opposite sides of the treatment volume in the patient.

The embodiments described above are merely given as examples, and it should be understood that the present invention is not limited thereto. Further modifications, changes and improvements that retain the basic underlying principles disclosed and claimed herein are within the scope and spirit of the invention.

What is claimed is:

1. A radiation system, comprising:
   a gantry including an inner gantry part and an outer gantry part;
   a radiation head mechanically supported by the inner gantry part and rotatable around a rotation axis, said radiation head comprising a treatment radiation source, arranged to direct treatment radiation to a treatment volume in an object; and a diagnostic imaging system, comprising:
  a diagnostic radiation source supported by the inner gantry part to direct diagnostic radiation onto the object,
  a detector unit responsive to both diagnostic radiation and treatment radiation passing through the object and outputting a signal representative of the detected radiation, and
  a processor, connected to the detector unit, for providing an image of the object based on the received output signal from the detector unit,
  wherein said inner gantry part is rotatably supported by the outer gantry part at two support locations situated, in the direction of the rotation axis, at opposite sides of the treatment volume.

2. The radiation system according to claim 1, wherein the diagnostic imaging system is a cone-beam computed tomography (CT) system and the diagnostic radiation source is adapted to emit the diagnostic radiation as cone-beam X-ray radiation.

3. The radiation system according to claim 1, wherein the detector unit and the diagnostic radiation source are rotatable around the rotation axis at a rotation speed adapted for computer tomography (CT) imaging.

4. The radiation system according to claim 1, wherein the treatment volume is situated substantially on the rotation axis.

5. The radiation system according to claim 1, wherein the diagnostic radiation source is arranged in or on the radiation head.

6. The radiation system according to claim 1, wherein the detector unit includes a stack of multiple converters, each converter being adapted for interaction with incident radiation to cause the emission of electrons into holes defined in the converter, holes of one of the converters being staggered with respect to holes of another one of the converters to provide high absorption efficiency for incident radiation while maintaining transparency for emitted electrons.

7. The radiation system according to claim 1, wherein the detector unit includes a sensor responsive to incident radiation, said sensor in turn comprising:
  a number of circuit boards each defined by two main surfaces and at least one edge surface, the area of the edge surface being substantially smaller than the area of the main surfaces;
  a set of radiation sensitive elements arranged at or in the vicinity of at least one edge surface of respective circuit board; and
  connection lines arranged on at least one of the main surfaces of respective circuit board for connecting the radiation sensitive elements to signal processing means;
  the circuit boards arranged adjacent to each other such that the sets of radiation sensitive elements form a sensor surface.

8. The radiation system according to claim 1, wherein the detector unit includes a sensor responsive to incident radiation, said sensor in turn comprising:
  a number of circuit boards each defined by two main surfaces and at least one edge surface, the area of the edge surface being substantially smaller than the area of the main surfaces;
  a set of radiation sensitive elements arranged on respective circuit board such that, in operation, the edge surface and an active surface of each of the radiation sensitive elements are facing the incident radiation; and
  connection lines arranged on at least one of the main surfaces of respective circuit board for connecting the radiation sensitive elements to signal processing means;
  the circuit boards arranged adjacent to each other such that the sets of radiation sensitive elements form a sensor surface.

9. The radiation system according to claim 1, wherein the radiation head is movable along at least one arc of a circle, substantially centered at the treatment volume.

10. The radiation system according claim 1, wherein the inner gantry part comprises a first ring portion and a second ring portion separated in the direction of the rotation axis, said ring portions are carried in a first support portion and a second support portion of said outer gantry part, respectively.

11. The radiation system according to claim 1, wherein the inner gantry part further comprises a first circle arc portion, on which the radiation head is movable, whereby the center of curvature of the first arc portion is situated in the treatment volume.

12. The radiation system according to claim 11, wherein the inner gantry part further comprises a second circle arc portion, arranged on the opposite side of the first rotation axis as compared to the first circle arc portion, on which the detector unit is movable, whereby the center of curvature of the second arc portion is situated in the treatment volume.

13. The radiation system according to claim 1, wherein the inner gantry part comprises a ring portion carried in a first support portion and a second support portion of said outer gantry part.

* * * * *